US006970239B2

(12) United States Patent
Chan et al.

(10) Patent No.: US 6,970,239 B2
(45) Date of Patent: Nov. 29, 2005

(54) METAL COATED NANOCRYSTALLINE SILICON AS AN ACTIVE SURFACE ENHANCED RAMAN SPECTROSCOPY (SERS) SUBSTRATE

(75) Inventors: Selena Chan, Sunnyvale, CA (US); Andrew A. Berlin, San Jose, CA (US); Mineo Yamakawa, Campbell, CA (US)

(73) Assignee: Intel Corporation, Santa Clara, CA (US)

( * ) Notice: Subject to any disclaimer, the term of this patent is extended or adjusted under 35 U.S.C. 154(b) by 132 days.

(21) Appl. No.: 10/171,357

(22) Filed: Jun. 12, 2002

(65) Prior Publication Data

US 2003/0231304 A1 Dec. 18, 2003

(51) Int. Cl.[7] .................................................. G01J 3/44
(52) U.S. Cl. ...................................................... 356/301
(58) Field of Search ................................ 356/301, 244

(56) References Cited

U.S. PATENT DOCUMENTS

| | | | |
|---|---|---|---|
| 5,255,067 A | 10/1993 | Carrabba et al. | |
| 5,306,403 A | 4/1994 | Vo-Dinh | |
| 5,561,304 A | 10/1996 | Canham et al. | |
| 5,770,022 A | 6/1998 | Chang et al. | |
| 5,994,164 A | 11/1999 | Fonash et al. | |
| 6,002,471 A | 12/1999 | Quake | |
| 6,017,773 A | 1/2000 | Fauchet et al. | |
| 6,040,191 A | 3/2000 | Grow | |
| 6,136,704 A | 10/2000 | Maya | |
| 6,149,868 A | 11/2000 | Natan et al. | |
| 6,153,489 A | 11/2000 | Park et al. | |
| 6,171,945 B1 | 1/2001 | Mandal et al. | |
| 6,174,677 B1 | 1/2001 | Vo-Dinh | |
| 6,180,415 B1 | 1/2001 | Schultz et al. | |
| 6,249,080 B1 | 6/2001 | Komoda et al. | |

(Continued)

FOREIGN PATENT DOCUMENTS

| | | | |
|---|---|---|---|
| EP | 0984269 A1 | 3/2000 | |
| WO | WO-00/08445 | * 2/2000 | .......... G01N/21/65 |

OTHER PUBLICATIONS

Unal, et al. "Photovoltaic Properties of a Novel Stain Etched Porous Silicon and its Application in Photosensitive Devices," *Optical Materials*, 17(2001) 79–82.

Vo–Dinh, "Surface–Enhanced Raman Spectroscopy Using Metallic Nanostructures," *Trends in Analytical Chemistry*, vol. 17, Nos. 8–9, 1998.

Cai, et al., "Optical Properties of Ag and Au Nanoparticles Dispersed within the Pores of Monolithic Mesoporous Silica," *J. Nanoparticle Res.* 3:443–453, 2001.

Cai, et al., "Direct Formation of Self–Assembled Nanoporous Aluminium Oxide in $SiO_2$ and Si Substrates," *Nanotechnology* 13:627, 2002.

(Continued)

*Primary Examiner*—F. L. Evans
*Assistant Examiner*—Kara Geisel
(74) *Attorney, Agent, or Firm*—DLA Piper Rudnick Gray Cary US LLP

(57) ABSTRACT

The methods and apparatus 300 disclosed herein concern Raman spectroscopy using metal coated nanocrystalline porous silicon substrates 240, 340. In certain embodiments of the invention, porous silicon substrates 110, 210 may be formed by anodic etching in dilute hydrofluoric acid 150. A thin coating of a Raman active metal, such as gold or silver, may be coated onto the porous silicon 110, 210 by cathodic electromigration or any known technique. The metal-coated substrate 240, 340 provides an extensive, metal rich environment for SERS, SERRS, hyper-Raman and/or CARS Raman spectroscopy. In certain embodiments of the invention, metal nanoparticles may be added to the metal-coated substrate 240, 340 to further enhance the Raman signals. Raman spectroscopy may be used to detect, identify and/or quantify a wide variety of analytes, using the disclosed methods and apparatus 300.

25 Claims, 3 Drawing Sheets

U.S. PATENT DOCUMENTS

| | | | |
|---|---|---|---|
| 6,268,041 B1 | 7/2001 | Goldstein | |
| 6,294,442 B1 | 9/2001 | Kamal | |
| 6,300,193 B1 | 10/2001 | Forbes | |
| 6,312,768 B1 | 11/2001 | Rode et al. | |
| 6,313,914 B1 | 11/2001 | Roe | |
| 6,322,895 B1 | 11/2001 | Canham | |
| 6,344,272 B1 | 2/2002 | Oldenburg et al. | |
| 6,358,613 B1 | 3/2002 | Buriak | |
| 6,358,815 B2 | 3/2002 | Maeda | |
| 6,359,276 B1 | 3/2002 | Tu | |
| 6,376,177 B1 | 4/2002 | Poponin | |
| 6,399,177 B1 | 6/2002 | Fonash et al. | |
| 6,478,974 B1 | 11/2002 | Lebouitz et al. | |
| 6,623,977 B1 * | 9/2003 | Farquharson et al. | 356/301 |
| 2002/0142480 A1 * | 10/2002 | Natan | 356/301 |

OTHER PUBLICATIONS

Chan, et al., "Tunable, Narrow, and Directional Luminescence From Porous Silicon Light Emitting Devices," *Applied Physics Lett.* 75:274–276, 1999.

Duffy, et al., "Rapid Prototyping of Microfludidic Systems in Poly(dimethylsiloxane)," *Anal. Chem.* 70:4974–84, 1998.

Varghese, et al., "Highly Ordered Nanoporous Alumina Films: Effect of Pore Size and Uniformity on Sensing Performance," *J. Mater. Res.* 17:1162–1171, 2002.

Weiping, et al. "Synthesis and Structural and Optical Properties of Mesoporous Silica Containing Silver Nanoparticles," *J. Phys. Condens. Matter* 9:7257–67, 1997.

Schoenfeld, et al., "Formation of Si Quantum Dots in Nanocrystalline Silicon," Proc. 7$^{th}$ Int. Conf. On Modulated Semiconductor Structures, Madrid, pp. 605–608, 1995.

Canham, "Silicon quantum wire array fabrication by electrochemical and chemical dissolution of wafers," Appl. Phys. Lett. 57:1046, 1990.

Collins et al., Physics Today 50:24–31, 1997.

Cullis et al., J. Appl. Phys. 82:909–965, 1997.

Edelberg, et al., "Visible luminescence from nanocrystalline silicon films produced by plasma enhanced chemical vapor deposition," Appl. Phys. Lett., 68:1415–1417, 1996.

Feldheim, "Assembly of metal nanoparticle arrays using molecular bridges," The Electrochemical Society Interface, Fall, 2001, pp. 22–25.

Gole et al., "Patterned metallization of porous silicon from electroless solution for direct electrical contact," J. Electrochem. Soc. 147:3785, 2000.

Henneke, "Porous Silicon: theories behind light emission," 1996, 1–4. Retrieved from the Internet URL: <http://neon.utexas.edu/academic/courses/Fall1997/CH380L/student.papers/dh.html>.

Jin et al., "Photoinduced conversion of silver nanospheres to nanoprisms," *Science* 294:1901, 2001.

Lopez and Fauchet, "Erbium emission from porous silicon one-dimensional photonic band gap structures," Appl. Phys. Lett. 77:3704–6, 2000.

Lutzen et al., Structural characteristics of ultrathin nanocrystalline silicon films formed by annealing amorphous silicon, J. Vac. Sci. Technology B 16:2802–05, 1998.

Petrova–Koch et al., "Rapid–thermal–oxidized porous silicon—the superior photoluminescent Si," Appl. Phys. Lett. 61:943, 1992.

* cited by examiner

METAL COATED NANOCRYSTALLINE SILICON AS AN ACTIVE SURFACE ENHANCED RAMAN SPECTROSCOPY (SERS) SUBSTRATE

FIELD OF THE INVENTION

The present methods and apparatus 300 relate to the fields of molecular detection and/or characterization by Raman spectroscopy. More particularly, the methods and apparatus 300 concern metal-coated porous silicon as a substrate 240, 340 for surface enhanced Raman spectroscopy (SERS), surface enhanced resonance Raman spectroscopy (SERRS), hyper-Raman and/or coherent anti-Stokes Raman spectroscopy (CARS).

BACKGROUND

The sensitive and accurate detection and/or identification of single molecules from biological and other samples has proven to be an elusive goal, with widespread potential uses in medical diagnostics, pathology, toxicology, environmental sampling, chemical analysis, forensics and numerous other fields. Attempts have been made to use Raman spectroscopy and/or surface plasmon resonance to achieve this goal. When light passes through a tangible medium, a certain amount becomes diverted from its original direction, a phenomenon known as Raman scattering. Some of the scattered light also differs in frequency from the original excitatory light, due to the absorption of light and excitation of electrons to a higher energy state, followed by light emission at a different wavelength. The wavelengths of the Raman emission spectrum are characteristic of the chemical composition and structure of the light absorbing molecules in a sample, while the intensity of light scattering is dependent on the concentration of molecules in the sample.

The probability of Raman interaction occurring between an excitatory light beam and an individual molecule in a sample is very low, resulting in a low sensitivity and limited applicability of Raman analysis. It has been observed that molecules near roughened silver surfaces show enhanced Raman scattering of as much as six to seven orders of magnitude. This surface enhanced Raman spectroscopy (SERS) effect is related to the phenomenon of plasmon resonance, wherein metal nanoparticles exhibit a pronounced optical resonance in response to incident electromagnetic radiation, due to the collective coupling of conduction electrons in the metal. In essence, nanoparticles of gold, silver, copper and certain other metals can function as miniature "antenna" to enhance the localized effects of electromagnetic radiation. Molecules located in the vicinity of such particles exhibit a much greater sensitivity for Raman spectroscopic analysis.

Attempts have been made to exploit SERS for molecular detection and analysis, typically by coating metal nanoparticles or fabricating rough metal films on the surface of a substrate and then applying a sample to the metal-coated surface. However, the number of metal particles that can be deposited on a planar surface is limited, producing a relatively low enhancement factor for SERS and related Raman techniques utilizing such surfaces. A need exists for methods of producing SERS-active substrates with higher densities of metal particles and apparatus comprising such substrates.

BRIEF DESCRIPTION OF THE DRAWINGS

The following drawings form part of the present specification and are included to further demonstrate certain aspects of the disclosed embodiments of the invention. The embodiments of the invention may be better understood by reference to one or more of these drawings in combination with the detailed description of specific embodiments presented herein.

DESCRIPTION OF ILLUSTRATIVE EMBODIMENTS

Figure 1:
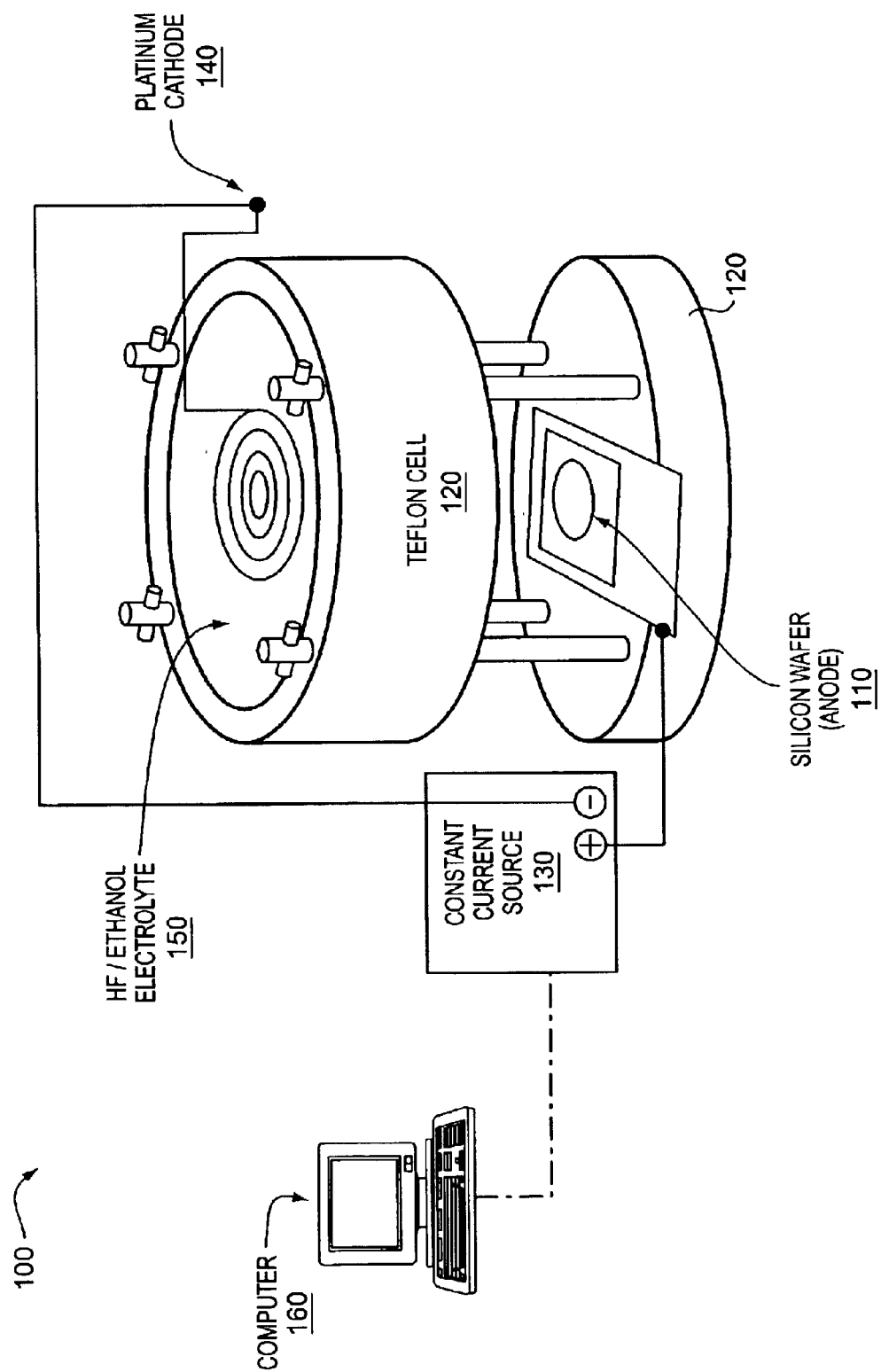
FIG. 1 illustrates an exemplary apparatus 100 (not to scale) and method for producing a porous silicon substrate 110.

The disclosed methods and apparatus 300 are of use for the detection and/or identification of analytes by surface enhanced Raman spectroscopy (SERS), surface enhanced resonance Raman spectroscopy (SERRS) and/or coherent anti-Stokes Raman spectroscopy (CARS) detection. Compared to existing techniques, the disclosed methods and apparatus 300 provide SERS active substrates 240, 340 with increased metal particle density and greater depth of field of SERS enhancement, allowing more efficient Raman detection and/or identification of analytes.

Previous methods for SERS detection of various analytes have used colloidal metal particles, such as aggregated silver nanoparticles, that were typically coated onto a substrate and/or support (e.g., U.S. Pat. Nos. 5,306,403; 6,149,868; 6,174,677; 6,376,177). While such arrangements occasionally allow SERS detection with as much as $10^6$ to $10^8$ increased sensitivity, they are not capable of single molecule detection of small analytes such as nucleotides, as disclosed herein. Enhanced sensitivity of Raman detection is apparently not uniform within a colloidal particle aggregate, but rather depends on the presence of "hot spots." The physical structure of such hot spots, the range of distances from the nanoparticles at which enhanced sensitivity occurs, and the spatial relationships between aggregate nanoparticles and analytes that allow enhanced sensitivity have not been characterized. Further, aggregated nanoparticles are inherently unstable in solution, with adverse effects on the reproducibility of single molecule analyte detection. The present methods and apparatus 300 provide a stable microenvironment for SERS detection in which the physical conformation and density of the Raman-active metal substrate may be precisely controlled, allowing reproducible, sensitive and accurate detection of analytes in solution.

The following detailed description contains numerous specific details in order to provide a more thorough understanding of the disclosed embodiments of the invention. However, it will be apparent to those skilled in the art that the embodiments of the invention may be practiced without these specific details. In other instances, devices, methods, procedures, and individual components that are well known in the art have not been described in detail herein.

Definitions

As used herein, "a" or "an" may mean one or more than one of an item.

As used herein, "about" means within ten percent of a value. For example, "about 100" would mean a value between 90 and 110.

As used herein, the term "analyte" means any atom, chemical, molecule, compound, composition or aggregate of interest for detection and/or identification. Non-limiting examples of analytes include an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product and/or contaminant. In certain embodiments of the invention, one or more analytes may be labeled with one or more Raman labels, as disclosed below.

A "capture" molecule is used herein to mean any molecule that may bind to one or more target analytes. Non-limiting examples of "capture" molecules include antibodies, antibody fragments, genetically engineered antibodies, single chain antibodies, receptor proteins, binding proteins, enzymes, inhibitor proteins, lectins, cell adhesion proteins, oligonucleotides, polynucleotides, nucleic acids and aptamers.

As used herein, the term "nanocrystalline silicon" refers to silicon that comprises nanometer-scale silicon crystals, typically in the size range from 1 to 100 nanometers (nm). "Porous silicon" 110, 210 refers to silicon that has been etched or otherwise treated to form a porous structure.

As used herein, "operably coupled" means that there is a functional interaction between two or more units of an apparatus 300 and/or system. For example, a Raman detector 380 may be "operably coupled" to a computer 160, 395 if the computer 160, 395 can obtain, process, store and/or transmit data on Raman signals detected by the detector 380.

Nanocrystalline Porous Silicon
Nanocrystalline Silicon

Certain embodiments of the invention concern apparatus 300 comprising one or more layers of nanocrystalline silicon. Various methods for producing nanocrystalline silicon are known in the art (e.g., Petrova-Koch et al., "Rapid-thermal-oxidized porous silicon—the superior photoluminescent Si," Appl. Phys. Lett. 61:943, 1992; Edelberg, et al., "Visible luminescence from nanocrystalline silicon films produced by plasma enhanced chemical vapor deposition," Appl. Phys. Lett., 68:1415–1417, 1996; Schoenfeld, et al., "Formation of Si quantum dots in nanocrystalline silicon," Proc. 7Int. Conf. on Modulated Semiconductor Structures, Madrid, pp. 605–608, 1995; Zhao, et al., "Nanocrystalline Si: a material constructed by Si quantum dots," 1st Int. Conf. on Low Dimensional Structures and Devices, Singapore, pp. 467–471, 1995; Lutzen et al., Structural characteristics of ultrathin nanocrystalline silicon films formed by annealing amorphous silicon, J. Vac. Sci. Technology B 16:2802–05, 1998; U.S. Pat. Nos. 5,770,022; 5,994,164; 6,268,041; 6,294,442; 6,300,193). The methods and apparatus 300 disclosed herein are not limited by the method of producing nanocrystalline silicon and it is contemplated that any known method may be used.

Non-limiting exemplary methods for producing nanocrystalline silicon include silicon (Si) implantation into a silicon rich oxide and annealing; solid phase crystallization with metal nucleation catalysts; chemical vapor deposition; PECVD (plasma enhanced chemical vapor deposition); gas evaporation; gas phase pyrolysis; gas phase photopyrolysis; electrochemical etching; plasma decomposition of silanes and polysilanes; high pressure liquid phase reduction-oxidation reactions; rapid annealing of amorphous silicon layers; depositing an amorphous silicon layer using LPCVD (low pressure chemical vapor deposition) followed by RTA (rapid thermal anneal) cycles; plasma electric arc deposition using a silicon anode and laser ablation of silicon (U.S. Pat. Nos. 5,770,022; 5,994,164; 6,268,041; 6,294,442; 6,300, 193). Depending on the process, Si crystals of anywhere from 1 to 100 nm or more in size may be formed as a thin layer on a chip, a separate layer and/or as aggregated crystals. In certain embodiments of the invention, a thin layer comprising nanocrystalline silicon attached to a substrate layer 110, 210 may be used.

Figure 2:
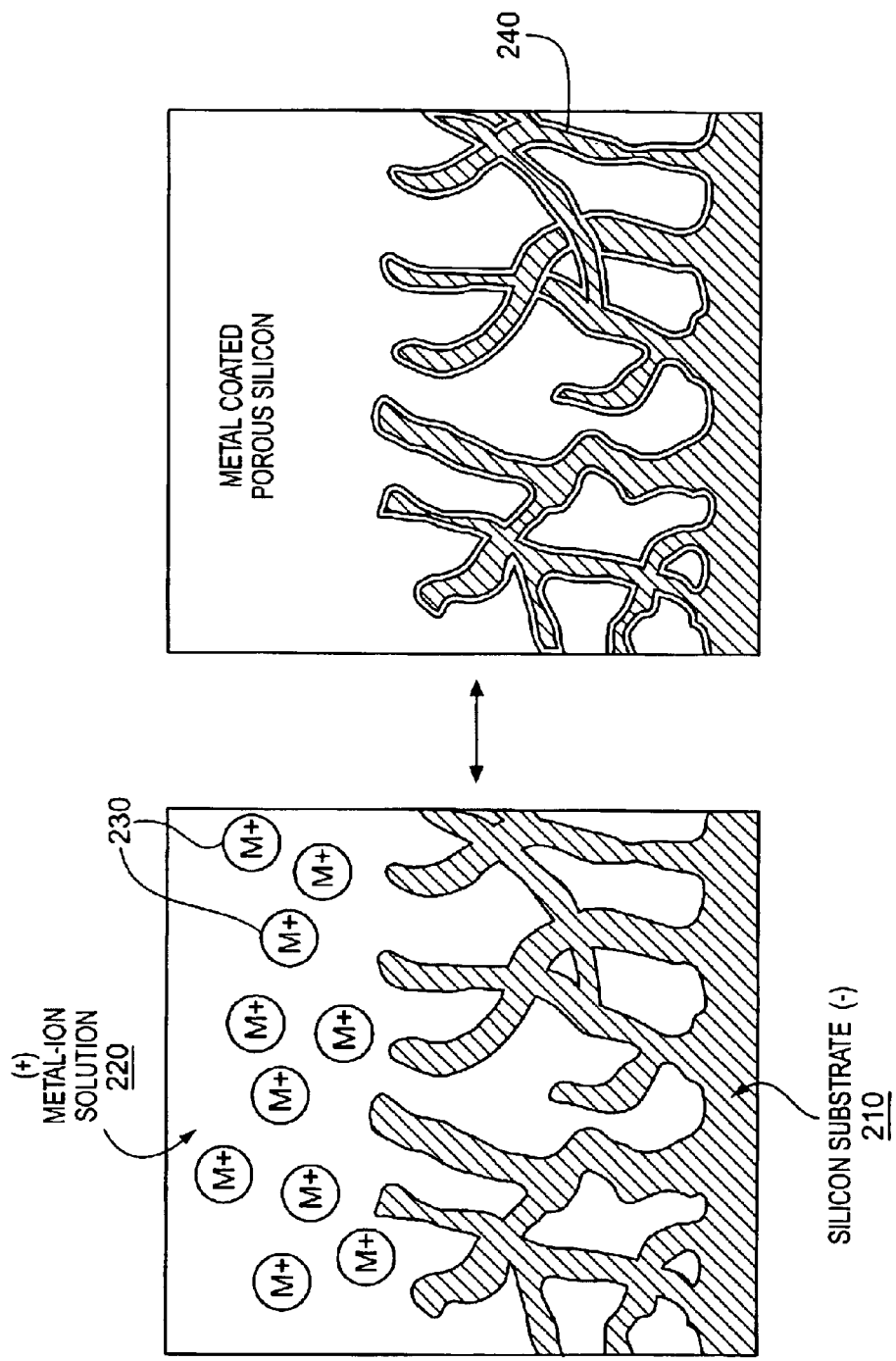
FIG. 2 illustrates an exemplary method for producing a metal-coated porous silicon substrate 240, 340.

In various embodiments of the invention, it is contemplated that nanocrystalline silicon may be used in the disclosed methods and apparatus 300. However, the embodiments are not limited to as to the composition of the starting material, and in alternative embodiments of the invention it is contemplated that other materials may be utilized, the only requirement being that the material must be capable of forming a porous substrate 110, 210 that can be coated with a Raman sensitive metal, as exemplified in FIG. 2.

In certain embodiments of the invention, the size and/or shape of silicon crystals and/or pore size in porous silicon may be selected to be within predetermined limits, for example, in order to optimize the plasmon resonant frequency of metal-coated porous silicon 240, 340 (see, e.g., U.S. Pat. No. 6,344,272). The plasmon resonant frequency may also be adjusted by controlling the thickness of the metal layer coating the porous silicon 240, 340 (U.S. Pat. No. 6,344,272). Techniques for controlling the size of nanoscale silicon crystals are known (e.g., U.S. Pat. Nos. 5,994, 164 and 6,294,442).

Porous Silicon

Certain embodiments of the invention concern apparatus 300 comprising and methods of use a Raman active, metal-coated substrate 240, 340. In various embodiments, the substrate comprises nanocrystalline porous silicon 110, 210. As discussed above, the substrate 110, 210 is not limited to pure silicon, but may also comprise silicon nitride, germanium and/or other materials known for chip manufacture. Other minor amounts of material may also be present, such as metal nucleation catalysts and/or dopants. The only requirement is that the substrate material must be capable of forming a porous substrate 110, 210 that can be coated with a Raman sensitive metal, as exemplified in FIG. 2. Porous silicon has a large surface area of up to 783 $m^2/cm^3$, providing a very large surface for surface enhanced Raman spectroscopy techniques.

Porous silicon 110, 210 was discovered in the late 1950's by electropolishing silicon in dilute hydrofluoric acid solutions. As is known in the art, porous silicon 110, 210 may be produced by etching of a silicon substrate 110, 210 with dilute hydrofluoric acid (HF) 150 in an electrochemical cell 120. In certain cases, silicon may be initially etched in HF 150 at low current densities. After the initial pores are formed, the silicon may be removed from the electrochemical cell 120 and etched in very dilute HF 150 to widen the pores formed in the electrochemical cell 120. The composition of the silicon substrate 110, 210 will also affect pore size, depending on whether or not the silicon is doped, the type of dopant and the degree of doping. The effect of doping on silicon pore size is known in the art. For embodiments of the invention involving detection and/or identification of large biomolecules, a pore size of about 2 nm to 100 or 200 nm may be selected. The orientation of pores in porous silicon may also be selected in particular embodiments of the invention. For example, an etched 1,0,0 crystal structure will have pores oriented perpendicular to the crystals, while 1,1,1 or 1,1,0 crystal structures will have pores oriented diagonally along the crystal axis. The effect of crystal structure on pore orientation is also known in the art. Crystal composition and porosity may also be regulated to change the optical properties of the porous silicon in order to enhance the Raman signals and decrease background noise. Optical properties of porous silicon are well known in the art (e.g., Cullis et al., J. Appl. Phys. 82:909–965, 1997; Collins et al., Physics Today 50:24–31, 1997).

A non-limiting example of a method and apparatus 100 for producing a porous silicon substrate 110, 210 is illustrated in FIG. 1. A silicon wafer 110 is placed inside an electrochemical cell 120 comprising an inert material, such as Teflon®. The wafer 110 is connected to the positive pole of a constant current source 130, thus forming the anode 110 of the electrochemical cell 120. The negative pole of the constant current source 130 is connected to a cathode 140, such as a platinum cathode 140. The electrochemical cell 120 may be filled with a dilute electrolyte solution of HF in ethanol 150. Alternatively, HF 150 may be dissolved in other alcohols and/or surfactants known in the art, such as pentane or hexane. In certain embodiments of the invention, a computer 160, 395 may be operably coupled to a constant current source 130 to regulate the current, voltage and/or time of electrochemical etching. The silicon wafer 110 exposed to HF electrolyte 150 in the electrochemical cell 120 becomes etched to form a porous silicon substrate 110, 210. As is known in the art, the thickness of the porous silicon layer 210 and the degree of porosity of the silicon 210 may be controlled by regulating the time and/or current density of anodization and the concentration of HF 150 in the electrolyte solution (e.g., U.S. Pat. No. 6,358,815).

In various embodiments of the invention, portions of the silicon wafer 110 may be protected from HF 150 etching by coating with any known resist compound, such as polymethyl-methacrylate. Lithography methods, such as photolithography, of use for exposing selected portions of a silicon wafer 110 to HF 150 etching are well known in the art. Selective etching may be of use to control the size and shape of a porous Si chamber to be used for Raman spectroscopy. In certain embodiments of the invention, a porous silicon chamber of about 1 $\mu$m (micrometer) in diameter may be used. In other embodiments of the invention, a trench or channel of porous silicon of about 1 $\mu$m in width may be used. The size of the porous silicon chamber is not limiting, and it is contemplated that any size or shape of porous silicon chamber may be used. A 1 $\mu$m chamber size may be of use, for example, with an excitatory laser that is 1 $\mu$m in size.

The exemplary method disclosed above is not limiting for producing porous silicon substrates 110, 210 and it is contemplated that any method known in the art may be used. Non-limiting examples of methods for making porous silicon substrates 110, 210 include anodic etching of silicon wafers 110; electroplating; and depositing a silicon/oxygen containing material followed by controlled annealing; (e.g., Canham, "Silicon quantum wire array fabrication by electrochemical and chemical dissolution of wafers," Appl. Phys. Lett. 57:1046, 1990; U.S. Pat. Nos. 5,561,304; 6,153, 489; 6,171,945; 6,322,895; 6,358,613; 6,358,815; 6,359, 276). In various embodiments of the invention, the porous silicon layer 210 may be attached to one or more supporting layers, such as bulk silicon, quartz, glass and/or plastic. In certain embodiments, an etch stop layer, such as silicon nitride, may be used to control the depth of etching. The porous silicon layer 210 may be incorporated into a semiconductor chip, using known methods of chip manufacture. In certain embodiments of the invention, the metal-coated porous silicon 240, 340 chamber may be designed as part of an integral chip, connected to various channels, microchannels, nanochannels, microfluidic channels, reaction chambers, etc. In alternative embodiments, the metal-coated porous silicon 240, 340 chamber may be cut out of a silicon wafer and incorporated into a chip and/or other device.

In certain alternative embodiments of the invention, it is contemplated that additional modifications to the porous silicon substrate 110, 210 may be made, either before or after metal coating. For example, after etching a porous silicon substrate 110, 210 may be oxidized, using methods known in the art, to silicon oxide and/or silicon dioxide. Oxidation may be used, for example, to increase the mechanical strength and stability of the porous silicon substrate 110, 210. Alternatively, the metal-coated silicon substrate 240, 340 may be subjected to further etching to remove the silicon material, leaving a metal shell that may be left hollow or may be filled with other materials, such as additional Raman active metal.

Metal Coating of Porous Silicon

The porous silicon substrate 110, 210 may be coated with a Raman active metal, such as gold, silver, platinum, copper or aluminum, by any method known in the art. Non-limiting exemplary methods include electroplating; cathodic electromigration; evaporation and sputtering of metals; using seed crystals to catalyze plating (i.e. using a copper/nickel seed to plate gold); ion implantation; diffusion; or any other method known in the art for plating thin metal layers on a silicon substrate 110, 210, 240, 340. (See, e.g., Lopez and Fauchet, "Erbium emission form porous silicon one-dimensional photonic band gap structures," Appl. Phys. Lett. 77:3704–6, 2000; U.S. Pat. Nos. 5,561,304; 6,171,945; 6,359,276.) Another non-limiting example of metal coating comprises electroless plating (e.g., Gole et al., "Patterned metallization of porous silicon from electroless solution for direct electrical contact," J. Electrochem. Soc. 147:3785, 2000). The composition and/or thickness of the metal layer may be controlled to optimize the plasmon resonance frequency of the metal-coated porous silicon 240, 340.

In alternative embodiments of the invention, the Raman active substrate 240, 340 used for analyte detection may comprise a metal-coated, nanocrystalline, porous silicon substrate 240, 240, immobilized metal colloids, such as silver or gold nanoparticles, coated on a different type of substrate, and/or immobilized metal colloids coated on top of a metal-coated, nanocrystalline, porous silicon substrate 240, 240. The latter composition would have a very high density of Raman active metal, with relatively small channels for analytes in solution to enter the substrate. Although this may be less favorable for large analyte molecules, such as large proteins or nucleic acids, it may provide better sensitivity and detection of small analytes, such as single nucleotides or amino acids. Metal colloids may be in the form of nanoparticles, as discussed below.

Nanoparticles

In certain embodiments of the invention, Raman active metal particles, such as gold or silver nanoparticles, may be added to the metal-coated porous silicon substrate 240, 340 to further enhance the Raman signal. In various embodiments of the invention, nanoparticles of between 1 nm and 2 $\mu$m in diameter may be used. In alternative embodiments of the invention, nanoparticles of 2 nm to 1 $\mu$m, 5 nm to 500 nm, 10 nm to 200 nm, 20 nm to 100 nm, 30 nm to 80 nm, 40 nm to 70 nm or 50 nm to 60 nm diameter are contemplated. In certain embodiments of the invention, nanoparticles with an average diameter of 10 to 50 nm, 50 to 100 nm or about 100 nm are contemplated. The size of the nanoparticles will depend on the diameter of the pores in the metal-coated porous silicon 240, 340 and may be selected so that the nanoparticles fit inside the pores. The nanoparticles may be approximately spherical in shape, although nanoparticles of any shape or of irregular shape may be used. Methods of preparing nanoparticles are known (e.g., U.S. Pat. Nos. 6,054,495; 6,127,120; 6,149,868; Lee and Meisel, *J. Phys. Chem.* 86:3391–3395, 1982). Nanoparticles may also be produced in the form of nanoprisms (Jin et al., "Photoinduced conversion of silver nanospheres to nanoprisms," *Science* 294:1901, 2001). Nanoparticles may be obtained from commercial sources (e.g., Nanoprobes Inc., Yaphank, N.Y.; Polysciences, Inc., Warrington, Pa.).

In certain embodiments of the invention, the nanoparticles may be random aggregates of nanoparticles (colloidal nanoparticles). In other embodiments of the invention, nanoparticles may be cross-linked to produce particular aggregates of nanoparticles, such as dimers, trimers, tetramers or other aggregates. Certain alternative embodiments of the invention may use heterogeneous mixtures of aggregates of different size, while other alternative embodiments may use homogenous populations of nanoparticle aggregates. In certain embodiments of the invention, aggregates containing a selected number of nanoparticles (dimers, trimers, etc.) may be enriched or purified by known techniques, such as ultracentrifugation in sucrose gradient solutions.

Methods of cross-linking nanoparticles are known in the art (see, e.g., Feldheim, "Assembly of metal nanoparticle arrays using molecular bridges," The Electrochemical Society Interface, Fall, 2001, pp. 22–25). Reaction of gold nanoparticles with linker compounds bearing terminal thiol or sulfhydryl groups is known (Feldheim, 2001). In some embodiments of the invention, a single linker compound may be derivatized with thiol groups at both ends. Upon reaction with gold nanoparticles, the linker would form nanoparticle dimers that are separated by the length of the linker. In other embodiments of the invention, linkers with three, four or more thiol groups may be used to simultaneously attach to multiple nanoparticles (Feldheim, 2001). The use of an excess of nanoparticles to linker compounds prevents formation of multiple cross-links and nanoparticle precipitation. Aggregates of silver nanoparticles may be formed by standard synthesis methods known in the art.

In particular embodiments of the invention, gold or silver nanoparticles may be coated with derivatized silanes, such as aminosilane, 3-glycidoxypropyltrimethoxysilane (GOP) or aminopropyltrimethoxysilane (APTS). The reactive groups at the ends of the silanes may be used to form cross-linked aggregates of nanoparticles. It is contemplated that the linker compounds used may be of almost any length, ranging from about 0.05, 0.1, 0.2, 0.5, 0.75, 1, 2, 3, 4, 5, 6, 7, 8, 9, 10, 11, 12, 13, 14, 15, 16, 17, 18, 19, 20, 21, 22, 23, 24, 25, 27, 30, 35, 40, 45, 50, 55, 60, 65, 70, 80, 90 to 100 nm or even greater length. Certain embodiments of the invention may use linkers of heterogeneous length.

In another alternative embodiment of the invention, the nanoparticles may be modified to contain various reactive groups before they are attached to linker compounds. Modified nanoparticles are commercially available, such as the Nanogold® nanoparticles from Nanoprobes, Inc. (Yaphank, N.Y.). Nanogold® nanoparticles may be obtained with either single or multiple maleimide, amine or other groups attached per nanoparticle. The Nanogold® nanoparticles are also available in either positively or negatively charged form to facilitate manipulation of nanoparticles in an electric field. Such modified nanoparticles may be attached to a variety of known linker compounds to provide dimers, trimers or other aggregates of nanoparticles.

The type of linker compound used is not limiting, so long as it results in the production of small aggregates of nanoparticles that will not precipitate in solution. In some embodiments of the invention, the linker group may comprise phenylacetylene polymers (Feldheim, 2001). Alternatively, linker groups may comprise polytetrafluoroethylene, polyvinyl pyrrolidone, polystyrene, polypropylene, polyacrylamide, polyethylene or other known polymers. The linker compounds of use are not limited to polymers, but may also include other types of molecules such as silanes, alkanes, derivatized silanes or derivatized alkanes. In particular embodiments of the invention, linker compounds of relatively simple chemical structure, such as alkanes or silanes, may be used to avoid interfering with the Raman signals emitted by analytes Micro-Electro-Mechanical Systems (MEMS)

In some embodiments of the invention, the Raman active metal-coated porous silicon substrate 240, 340 may be incorporated into a larger apparatus 300 and/or system. In certain embodiments, the substrate 240, 340 may be incorporated into a micro-electro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (e.g., Voldman et al., *Ann. Rev. Biomed. Eng.* 1:401–425, 1999). The sensor components of MEMS may be used to measure mechanical, thermal, biological, chemical, optical and/or magnetic phenomena. The electronics may process the information from the sensors and control actuator components such pumps, valves, heaters, coolers, filters, etc. thereby controlling the function of the MEMS.

The electronic components of MEMS may be fabricated using integrated circuit (IC) processes (e.g., CMOS, Bipolar, or BICMOS processes). They may be patterned using photolithographic and etching methods known for computer chip manufacture. The micromechanical components may be fabricated using compatible "micromachining" processes that selectively etch away parts of the silicon wafer or add new structural layers to form the mechanical and/or electromechanical components.

Basic techniques in MEMS manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. Methods for manufacture of nanoelectromechanical systems may be used for certain embodiments of the invention. (See, e.g., Craighead, *Science* 290:1532–36, 2000.)

In some embodiments of the invention, the metal-coated porous silicon substrate 240, 340 may be connected to various fluid filled compartments, such as microfluidic channels, nanochannels and/or microchannels. These and other components of the apparatus 300 may be formed as a single unit, for example in the form of a chip as known in semiconductor chips and/or microcapillary or microfluidic chips. Alternatively, the metal-coated porous silicon substrate 240, 340 may be removed from a silicon wafer and attached to other components of an apparatus 300. Any materials known for use in such chips may be used in the disclosed apparatus 300, including silicon, silicon dioxide, silicon nitride, polydimethyl siloxane (PDMS), polymethylmethacrylate (PMMA), plastic, glass, quartz, etc.

Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Methods for manufacture of nanoelectromechanical systems may be used for certain embodiments of the invention. (See, e.g., Craighead, Science 290:1532–36, 2000.) Various forms of microfabricated chips are commercially available from, e.g., Caliper Technologies Inc. (Mountain View, Calif.) and ACLARA BioSciences Inc. (Mountain View, Calif.).

In certain embodiments of the invention, part or all of the apparatus 300 may be selected to be transparent to electromagnetic radiation at the excitation and emission frequencies used for Raman spectroscopy, such as glass, silicon, quartz or any other optically clear material. For fluid-filled compartments that may be exposed to various biomolecules, such as proteins, peptides, nucleic acids, nucleotides and the like, the surfaces exposed to such molecules may be modified by coating, for example to transform a surface from a hydrophobic to a hydrophilic surface and/or to decrease adsorption of molecules to a surface. Surface modification of common chip materials such as glass, silicon, quartz and/or PDMS is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other coating known in the art.

Raman Spectroscopy
Raman Detectors

In some embodiments of the invention, analytes may be detected and/or identified by any known method of Raman spectroscopy. In such embodiments, the Raman active substrate 240, 340 may be operably coupled to one or more Raman detection units 360. Various methods for detection of analytes by Raman spectroscopy are known in the art. (See, e.g., U.S. Pat. Nos. 6,002,471; 6,040,191; 6,149,868; 6,174,677; 6,313,914). Variations on surface enhanced Raman spectroscopy (SERS), surface enhanced resonance Raman spectroscopy (SERRS), hyper-Raman spectroscopy and coherent anti-Stokes Raman spectroscopy (CARS) have been disclosed. In SERS and SERRS, the sensitivity of the Raman detection is enhanced by a factor of $10^6$ or more for molecules adsorbed on roughened metal surfaces, such as silver, gold, platinum, copper or aluminum surfaces.

A non-limiting example of a Raman detection unit 360 is disclosed in U.S. Pat. No. 6,002,471. An excitation beam 390 is generated by either a frequency doubled Nd:YAG laser 370 at 532 nm wavelength or a frequency doubled Ti:sapphire laser 370 at 365 nm wavelength. Pulsed laser beams 390 or continuous laser beams 390 may be used. The excitation beam 390 passes through confocal optics and a microscope objective, and is focused onto the Raman active substrate 240, 340 containing one or more analytes. The Raman emission light from the analytes is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector 380, comprising an avalanche photodiode interfaced with a computer 160, 395 for counting and digitization of the signal.

Another example of a Raman detection unit 360 is disclosed in U.S. Pat. No. 5,306,403, including a Spex Model 1403 double-grating spectrophotometer with a gallium-arsenide photomultiplier tube (RCA Model C31034 or Burle Industries Model C3103402) operated in the single-photon counting mode. The excitation source comprises a 514.5 nm line argon-ion laser 370 from SpectraPhysics, Model 166, and a 647.1 nm line of a krypton-ion laser 370 (Innova 70, Coherent).

Alternative excitation sources include a nitrogen laser 370 (Laser Science Inc.) at 337 nm and a helium-cadmium laser 370 (Liconox) at 325 nm (U.S. Pat. No. 6,174,677), a light emitting diode, an Nd:YLF laser 370, and/or various ions lasers 370 and/or dye lasers 370. The excitation beam 390 may be spectrally purified with a bandpass filter (Corion) and may be focused on the Raman active substrate 240, 340 using a 6× objective lens (Newport, Model L6X). The objective lens may be used to both excite the analytes and to collect the Raman signal, by using a holographic beam splitter (Kaiser Optical Systems, Inc., Model HB 647-26N18) to produce a right-angle geometry for the excitation beam 390 and the emitted Raman signal. A holographic notch filter (Kaiser Optical Systems, Inc.) may be used to reduce Rayleigh scattered radiation. Alternative Raman detectors 380 include an ISA HR-320 spectrograph equipped with a red-enhanced intensified charge-coupled device (RE-ICCD) detection system (Princeton Instruments). Other types of detectors 380 may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection of analytes, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

Raman Labels

Certain embodiments of the invention may involve attaching a label to one or more analytes to facilitate their measurement by the Raman detection unit 360. Non-limiting examples of labels that could be used for Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, quantum dots, carbon nanotubes and fullerenes. These and other Raman labels may be obtained from commercial sources (e.g., Molecular Probes, Eugene, Oreg.; Sigma Aldrich Chemical Co., St. Louis, Mo.) and/or synthesized by methods known in the art.

Polycyclic aromatic compounds may function as Raman labels, as is known in the art. Other labels that may be of use for particular embodiments of the invention include cyanide, thiol, chlorine, bromine, methyl, phosphorus and sulfur. The use of labels in Raman spectroscopy is known (e.g., U.S. Pat. Nos. 5,306,403 and 6,174,677). The skilled artisan will realize that the Raman labels used should generate distinguishable Raman spectra and may be specifically bound to or associated with different types of analytes.

Labels may be attached directly to the analytes or may be attached via various linker compounds. Cross-linking reagents and linker compounds of use in the disclosed methods are known in the art. Raman labels that contain reactive groups designed to covalently react with other molecules, such as analytes, are commercially available (e.g., Molecular Probes, Eugene, Oreg.). Methods for preparing labeled analytes are known (e.g., U.S. Pat. Nos. 4,962,037; 5,405,747; 6,136,543; 6,210,896).

Computers

In certain embodiments of the invention, apparatus 100, 300 may comprise a computer 160, 395. The embodiments are not limiting for the type of computer 160, 395 used. An exemplary computer 160, 395 may comprise a bus for communicating information and a processor for processing information. In one embodiment, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, an X-scale or a Pentium Xeon® processor (Intel Corp., Santa Clara, Calif.). In various other embodiments of the invention, the processor may be based on Intel® architecture, such as Intel® IA-32 or Intel® IA-64 architecture. Alternatively, other processors may be used.

The computer 160, 395 may further comprise a random access memory (RAM) or other dynamic storage device, a read only memory (ROM) or other static storage and a data storage device such as a magnetic disk or optical disc and its corresponding drive. The computer 160, 395 may also comprise other peripheral devices known in the art, such a display device (e.g., cathode ray tube or Liquid Crystal Display), an alphanumeric input device (e.g., keyboard), a cursor control device (e.g., mouse, trackball, or cursor direction keys) and a communication device (e.g., modem, network interface card, or interface device used for coupling to Ethernet, token ring, or other types of networks).

In particular embodiments of the invention, the Raman detection unit 360 may be operably coupled to the computer 160, 395. Data from the detection unit 360 may be processed by the processor and data stored in the main memory. Data on emission profiles for standard analytes may also be stored in main memory or in ROM. The processor may compare the emission spectra from analytes in Raman active substrate 240, 340 to identify the type of analyte(s) in the sample. The processor may analyze the data from the detection unit 360 to determine the identity and/or concentration of various analytes. It is appreciated that a differently equipped computer 160, 395 may be used for certain implementations. Therefore, the configuration of the system may vary in different embodiments of the invention.

While the processes described herein may be performed under the control of a programmed processor, in alternative embodiments of the invention, the processes may be fully or partially implemented by any programmable or hardcoded logic, such as Field Programmable Gate Arrays (FPGAs), TTL logic, or Application Specific Integrated Circuits (ASICs), for example. Additionally, the disclosed methods may be performed by any combination of programmed general purpose computer 160, 395 components and/or custom hardware components.

Following the data gathering operation, the data will typically be reported to a data analysis operation. To facilitate the analysis operation, the data obtained by the detection unit 360 will typically be analyzed using a digital computer 160, 395 such as that described above. Typically, the computer 160, 395 will be appropriately programmed for receipt and storage of the data from the detection unit 360 as well as for analysis and reporting of the data gathered.

In certain embodiments of the invention, custom designed software packages may be used to analyze the data obtained from the detection unit 360. In alternative embodiments of the invention, data analysis may be performed, using a computer 160, 395 and publicly available software packages.

EXAMPLES

Example 1

Construction of a Raman Active Substrate
Formation of Porous Nanocrystalline Silicon An exemplary method and apparatus 100 for forming nanocrystalline porous silicon substrates 110, 210 is illustrated in FIG. 1. Methods for making nanocrystalline porous silicon are known in the art (e.g., U.S. Pat. No. 6,017,773). A layer of nanocrystalline porous silicon may be formed electrochemically as disclosed in Petrova-Koch et al. (Appl. Phys. Let. 61:943, 1992). Depending on the particular application, the silicon may be lightly or heavily p-doped or n-doped prior to etching to regulate the characteristics of the porous silicon substrate 110, 210. Single crystal silicon ingots may be fabricated by the well known Czochralski method (e.g., http://www.msil.ab.psiweb.com/english/msilhist4-e.html). A single crystal silicon wafer 110 may be treated with anodic etching in dilute HF/ethanol 150 to form a nanocrystalline porous silicon substrate 110, 210. Alternatively, chemical etching in a solution of HF, nitric acid and water 150 may be used without anodic etching.

The wafer may be coated with polymethyl-methacrylate resist or any other known resist compound before etching. A pattern for the nanocrystalline porous silicon substrate 110, 210 may be formed by standard photolithographic techniques. In different embodiments of the invention, the nanocrystalline porous substrate 110, 210 may be circular, trench shaped, channel shaped or of any other selected shape. In certain embodiments, multiple porous substrates 110, 210 may be formed on a single silicon wafer 110 to allow for multiple sampling channels and/or chambers for Raman analysis. Each sampling channel and/or chamber may be operably coupled to one or more Raman detectors 380.

After resist coating and lithography, the wafer 110 may be exposed to a solution 150 of between about 15 to 50 weight percent HF in ethanol and/or distilled water in an electrochemical cell 120 comprised of Teflon®, as disclosed in FIG. 1. In different embodiments of the invention, the entire resist coated wafer 110 may be immersed in an HF solution 150. In alternative embodiments, the wafer 110 may be held in place in the electrochemical cell 120, for example using a synthetic rubber washer, with only a portion of the wafer 110 surface exposed to the HF solution 150 (U.S. Pat. No. 6,322,895). In either case, the wafer 110 may be electrically connected to the positive pole of a constant current source 130 to form the anode 110 of the electrochemical cell 120. A platinum electrode may provide the cathode 140 for the cell 120. The wafer 110 may be etched using an anodization current density of between 5 to 250 milliamperes/cm$^2$ for between 5 seconds to 30 minutes in the dark, depending on the selected degree of porosity. In particular embodiments of the invention, a porosity of about 10%, 15%, 20%, 25%, 30%, 35%, 40%, 45%, 50%, 60%, 70%, 80% or 90% may be selected. As is known in the art, the anodization current density required to form porous silicon 110, 210 may depend in part on the type of silicon substrate 110 used, such as whether the substrate 110 is lightly or heavily p-doped or n-doped.

In other alternative embodiments of the invention, the nanocrystalline porous silicon substrate 110, 210 may be incorporated into a MEMS device comprising a variety of detectors, sensors, electrodes, other electrical components, mechanical actuators, etc. using known chip manufacturing techniques. In certain embodiments, such manufacturing procedures may occur before and/or after formation of the porous silicon substrate 110, 210 and/or coating with a Raman sensitive metal.

Metal Coating

The porous silicon 110, 210 may be coated with metal by cathodic electromigration using known techniques (Lopez and Fauchet, 2000). For the purposes of the present Example, silver is used for the metal coating, although other metals such as gold or platinum may be used. The porous silicon surface 110, 210 is cleaned and doped with silver by electromigration according to Lopez and Fauchet (Appl. Phys. Lett. 75:3989, 1999). The skilled artisan will realize that any known technique for forming a thin metal coat on a porous silicon substrate 110, 210 may be used in various embodiments of the invention.

Example 2

Raman Detection of Analytes

Figure 3:
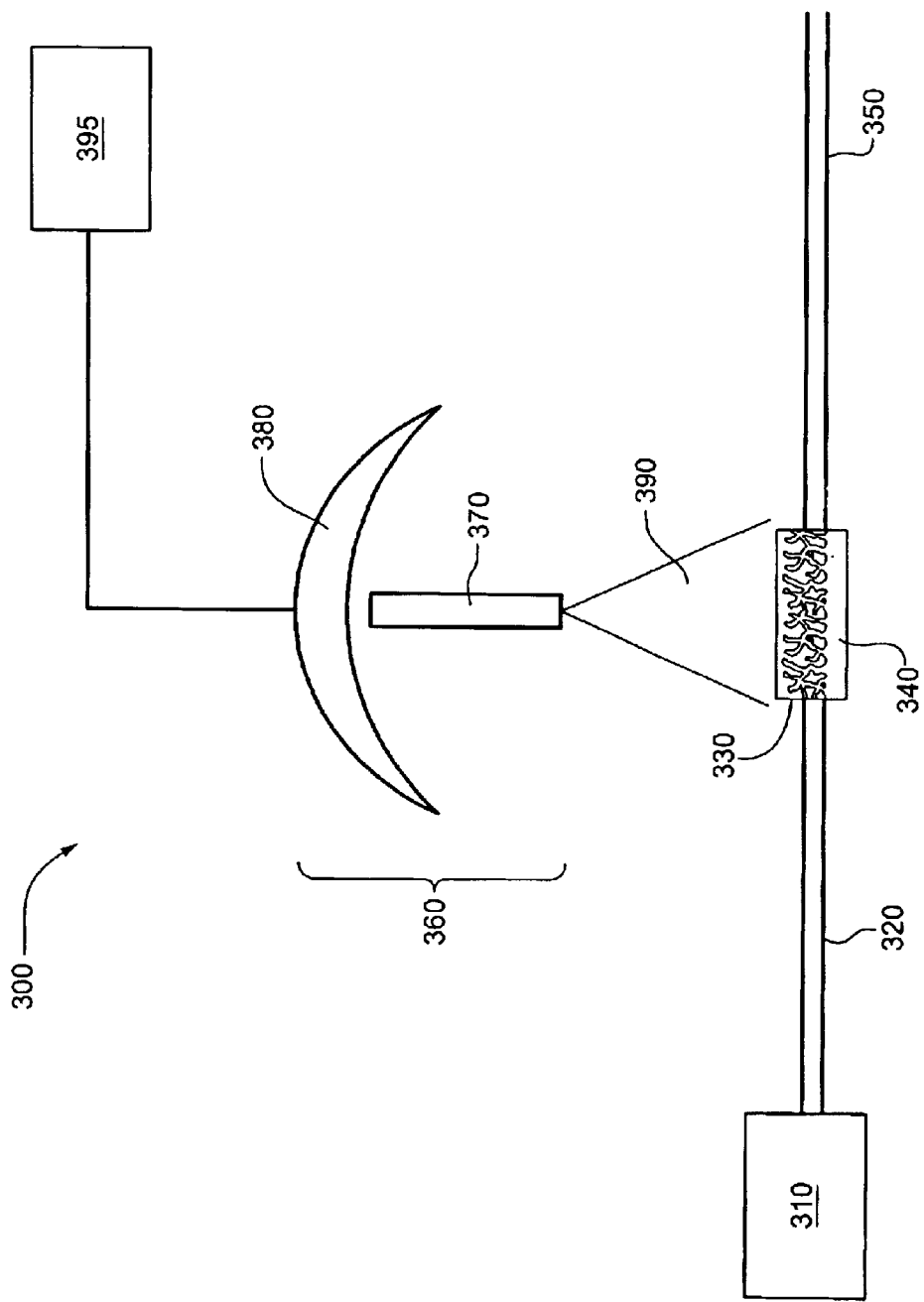
FIG. 3 illustrates an exemplary apparatus 300 and method for detecting and/or identifying analytes using a metal-coated SERS-active substrate 240, 340.

A Raman active metal-coated substrate 240, 340 formed as disclosed above may be incorporated into an apparatus 300 for Raman detection, identification and/or quantification of analytes, as exemplified in FIG. 3. The substrate 240, 340 may be incorporated into, for example, a flow through cell 330, connected to inlet 320 and outlet 350 channels. The inlet channel 320 may be connected to one or more other devices 310, such as a sample injector 310 and/or reaction chamber 310. Analytes may enter the flow through cell 330 and pass across the Raman active substrate 340, where they may be detected by a Raman detection unit 360. The detection unit 360 may comprise a Raman detector 380 and a light source 370, such as a laser 370. The laser 370 may emit an excitation beam 390, activating the analytes and resulting in emission of Raman signals. The Raman signals are detected by the detector 380. In certain embodiments of the invention, the detector 380 may be operably coupled to a computer 395 which can process, analyze, store and/or transmit data on analytes present in the sample.

In an exemplary embodiment of the invention, the excitation beam 390 is generated by a titanium:sapphire laser 370 (Tsunami by Spectra-Physics) at a near-infrared wavelength (750~950 nm) or a galium aluminum arsenide diode laser 370 (PI-ECL series by Process Instruments) at 785 nm or 830 nm. Pulsed laser beams 390 or continuous beams 390 may be used. The excitation beam 390 is reflected by a dichroic mirror (holographic notch filter by Kaiser Optical or an interference filter by Chroma or Omega Optical) into a collinear geometry with the collected beam. The reflected beam 390 passes through a microscope objective (Nikon LU series), and is focused onto the Raman active substrate 240, 340 where target analytes are located. The Raman scattered light from the analytes is collected by the same microscope objective, and passes the dichroic mirror to the Raman detector 380. The Raman detector 380 comprises a focusing lens, a spectrograph, and an array detector. The focusing lens focuses the Raman scattered light through the entrance slit of the spectrograph. The spectrograph (RoperScientific) comprises a grating that disperses the light by its wavelength. The dispersed light is imaged onto an array detector (back-illuminated deep-depletion CCD camera by RoperScientific). The array detector is connected to a controller circuit, which is connected to a computer 160, 395 for data transfer and control of the detector 380 function.

In various embodiments of the invention, the detection unit 360 is capable of detecting, identifying and/or quantifying a wide variety of analytes with high sensitivity, down to single molecule detection and/or identification. In certain embodiments of the invention, the analytes may comprise single nucleotides that may or may not be Raman labeled. In other embodiments, one or more oligonucleotide probes may or may not be labeled with distinguishable Raman labels and allowed to hybridize to target nucleic acids in a sample. The presence of a target nucleic acid may be indicated by hybridization with a complementary oligonucleotide probe and Raman detection using the apparatus 300 of FIG. 3. Alternatively, amino acids, peptides and/or proteins of interest may be detected and/or identified using the disclosed methods and apparatus 300. The skilled artisan will realize that the methods and apparatus 300 are not limiting as to the type of analytes that may be detected, identified and/or quantified, but rather that any analyte, whether labeled or unlabeled, that can be detected by Raman detection may be analyzed within the scope of the claimed subject matter.

In certain embodiments of the invention, one or more "capture" molecules may be attached either covalently or non-covalently to the Raman active substrate 240, 340 to enhance the sensitivity and/or specificity of Raman detection of analytes. For example, an oligonucleotide probe specific for a selected target nucleic acid could be attached to the metal surface of the substrate 240, 340 by known techniques. (E.g., an oligonucleotide may be covalently modified to contain a sulfhydryl moiety that can bond to a gold-coated substrate 240, 340.) Alternatively, an antibody specific for a target protein, peptide or other compound could be attached to the substrate 240, 240. The presence of a target analyte may be detected by exposing the oligonucleotide attached to the substrate 240, 340 to a sample under conditions allowing for hybridization to complementary nucleic acid sequences, followed by washing and then detection of bound analytes. In alternative embodiments of the invention, one or more analytes in a sample may be labeled with a distinguishable Raman label before exposure to the Raman active substrate 240, 340 to facilitate detection of bound analyte. Similar methods could be used with antibody-antigen pairs, ligand-receptor pairs or any other known pairs of analytes that exhibit selective and/or specific binding to each other. The substrate 240, 340 may be recycled and reused by treatment with various agents to remove bound analytes and/or capture molecules, such as washing with acid, water, organic solvent or detergent, chemical treatment and/or treatment with lytic enzymes such as exonucleases and/or proteases.

All of the METHODS and APPARATUS disclosed and claimed herein can be made and used without undue experimentation in light of the present disclosure. It will be apparent to those of skill in the art that variations may be applied to the METHODS and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. A method comprising:
   a) providing a crystalline porous substrate having a metal-coated contact surface;
   b) exposing the contact surface to a sample comprising one or more analytes so as to capture the analytes on the contact surface of the substrate; and
   c) using laser excitation and spectroscopy to detect and/or identify one or more of the analytes.

2. The method of claim 1 wherein the substrate is a porous semiconductor substrate.

3. The method of claim 2, wherein the substrate is selected from the group consisting of nanocrystalline silicon, single crystal silicon, and polycrystalline silicon.

4. The method of claim 1, wherein metal nanoparticles are added to the surface of the metal-coated substrate.

5. The method of claim 1, wherein in metal coating the contact surface comprises silver, gold, platinum, copper and/or aluminum.

6. The method of claim 1, wherein the spectroscopy is Raman spectroscopy.

7. The method of claim 6, wherein the Raman spectroscopy is surface enhanced Raman spectroscopy (SERS), surface enhanced resonance Raman spectroscopy (SERRS) hyper-Raman and/or coherent anti-Stokes Raman spectroscopy (CARS).

8. The method of claim 1, wherein the analyte is selected from the group consisting of an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, bacteria, virus, radioisotope, vitamin, heterocyclic aromatic compound, carcinogen, mutagen, narcotic, amphetamine, barbiturate, hallucinogen, waste product and contaminant.

9. The method of claim 8, wherein the analyte is a nucleoside, nucleotide, oligonucleotide, nucleic acid, amino acid, peptide, polypeptide or protein.

10. The method of claim 1, wherein the one or more analytes are labeled with one or more Raman labels.

11. The method of claim 10, wherein each analyte is labeled with a distinguishable Raman label.

12. The method of claim 3, wherein one or more capture molecules is attached to the metal-coated contact surface.

13. The method of claim 12, wherein the one or more capture molecules are selected from the group consisting of oligonucleotides, nucleic acids, antibodies, antibody fragments, antigens, epitopes, lectins, proteins, polypeptides, peptides, receptor proteins, ligands, hormones, vitamins, metabolites, substrates, inhibitors, cofactors, pharmaceuticals, aptamers, cytokines and neurotransmitters.

14. An apparatus comprising:
   a) a nanocrystalline porous silicon substrate having an upper porous surface coated with a metal;
   b) a laser;
   c) a Raman detector; and
   d) a spectrometer.

15. The apparatus of claim 14, wherein the porous silicon substrate is used as a support layer.

16. The apparatus of claim 15, wherein the support layer is replaced by a metal.

17. The apparatus of claim 14, further comprising metal nanoparticles touching the metal-coated surface.

18. The apparatus of claim 14, wherein the metal comprises silver, gold, platinum, copper and/or aluminum.

19. The apparatus of claim 14, further comprising a computer operably coupled to the Raman detector.

20. The apparatus of claim 14, further comprising a flow through cell operably coupled to the Raman detector, wherein flow passes through the nanocrystalline porous silicon substrate inside the flow through cell.

21. The apparatus of claim 14, wherein the metal-coated porous silicon substrate is incorporated into a micro-electro-mechanical system (MEMS).

22. The apparatus of claim 14, wherein the nanocrystalline silicon substrate is constructed as part of an integrated chip.

23. An apparatus of claim 20, wherein the nanocrystalline porous silicon substrate is removed from a wafer and incorporated into the MEMS.

24. The apparatus of claim 17, wherein the nanocrystalline substrate has at least one chamber or trench in the micron size range in the surface thereof.

25. The apparatus of claim 24, wherein the nanoparticles are nanoparticle aggregates or cross-linked nanoparticles.

* * * * *

UNITED STATES PATENT AND TRADEMARK OFFICE
CERTIFICATE OF CORRECTION

PATENT NO. : 6,970,239 B2  Page 1 of 1
APPLICATION NO. : 10/171357
DATED : November 29, 2005
INVENTOR(S) : Selena Chan et al.

It is certified that error appears in the above-identified patent and that said Letters Patent is hereby corrected as shown below:

In Claim 23, column 16, line 48, delete "20" and replace with --21--

Signed and Sealed this

Twenty-sixth Day of December, 2006

JON W. DUDAS
*Director of the United States Patent and Trademark Office*